United States Patent
Fattori

(10) Patent No.: US 9,775,693 B2
(45) Date of Patent: Oct. 3, 2017

(54) ORAL CARE IMPLEMENT

(71) Applicant: COLGATE-PALMOLIVE COMPANY, New York, NY (US)

(72) Inventor: Joseph E. Fattori, East Sandwich, MA (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 568 days.

(21) Appl. No.: 14/130,762

(22) PCT Filed: Dec. 3, 2013

(86) PCT No.: PCT/US2013/072859
§ 371 (c)(1),
(2) Date: Jan. 3, 2014

(87) PCT Pub. No.: WO2014/093059
PCT Pub. Date: Jun. 19, 2014

(65) Prior Publication Data
US 2015/0209125 A1 Jul. 30, 2015

Related U.S. Application Data

(60) Provisional application No. 61/735,650, filed on Dec. 11, 2012.

(51) Int. Cl.
*A61C 17/22* (2006.01)
(52) U.S. Cl.
CPC .......... *A61C 17/225* (2013.01); *A61C 17/222* (2013.01); *F04C 2270/0421* (2013.01)

(58) Field of Classification Search
CPC ................. A61C 17/225; A61C 17/222; F04C 2270/0421
(Continued)

(56) References Cited

U.S. PATENT DOCUMENTS 3,088,148 A * 5/1963 Moret ................... A61C 17/32
15/145
3,278,963 A * 10/1966 Bond ................. A61C 17/3418
132/119.1
(Continued)

FOREIGN PATENT DOCUMENTS

CN 201676033 12/2010
CN 102458298 5/2012
(Continued)

*Primary Examiner* — Marc Carlson

(57) ABSTRACT

An oral care implement, such as a toothbrush, which includes a handle and a replacement head utilizing a specially designed structure for coupling the replacement head to the handle of the oral care implement. The replacement head comprises a head and a tubular sleeve comprising a cavity for receiving a handle. A protuberance protrudes radially inward from an inner surface of the tubular sleeve for engaging a boss of a stem on the handle to impede rotation of the tubular sleeve about the stem in a first angular direction. A locking tab protrudes radially inward from the inner surface of the tubular sleeve for engaging an undercut surface of the boss to prevent axial disengagement of the tubular sleeve from the stem. The locking tab is circumferentially spaced from the protuberance so that a first axial channel exists therebetween for receiving a section of the boss.

22 Claims, 16 Drawing Sheets

(58) Field of Classification Search
USPC .............................................. 15/22.1, 143.1
See application file for complete search history.

(56) References Cited

U.S. PATENT DOCUMENTS

| | | | |
|---|---|---|---|
| 3,369,265 A * | 2/1968 | Halberstadt | A61C 17/32 |
| | | | 15/145 |
| 3,927,435 A | 12/1975 | Moret et al. | |
| 4,811,445 A | 3/1989 | Lagieski et al. | |
| 5,247,716 A | 9/1993 | Bock | |
| 5,365,627 A * | 11/1994 | Jousson | A46B 5/0095 |
| | | | 15/176.6 |
| 5,617,602 A | 4/1997 | Okada | |
| 5,727,273 A | 3/1998 | Pai | |
| 5,875,510 A | 3/1999 | Lamond et al. | |
| 6,015,328 A | 1/2000 | Glaser | |
| 6,161,244 A * | 12/2000 | Jeannet | A46B 5/0095 |
| | | | 15/145 |
| 6,202,242 B1 | 3/2001 | Salmon et al. | |
| 6,345,406 B1 | 2/2002 | Dodd | |
| 6,438,784 B1 | 8/2002 | Yu | |
| 6,536,066 B2 | 3/2003 | Dickie | |
| 6,546,585 B1 | 4/2003 | Blaustein et al. | |
| 7,137,166 B1 | 11/2006 | Kraemer | |
| 7,845,039 B2 | 12/2010 | Chan et al. | |
| 7,979,939 B2 | 7/2011 | Hilscher et al. | |
| 8,196,246 B1 * | 6/2012 | Haynes | A61C 17/222 |
| | | | 15/167.1 |
| 2002/0162180 A1 | 11/2002 | Blaustein et al. | |
| 2006/0168744 A1 | 8/2006 | Butler et al. | |
| 2007/0256262 A1 | 11/2007 | Moss | |
| 2010/0043156 A1 | 2/2010 | Kressner | |
| 2010/0269275 A1 * | 10/2010 | Shimoyama | A61C 17/3481 |
| | | | 15/22.1 |
| 2011/0010874 A1 | 1/2011 | Dickie | |
| 2012/0021382 A1 | 1/2012 | Dickie | |
| 2015/0020325 A1 | 1/2015 | Yoshida et al. | |

FOREIGN PATENT DOCUMENTS

| | | | |
|---|---|---|---|
| WO | WO2004019728 | 3/2004 | |
| WO | WO2004024021 | 3/2004 | |
| WO | WO 2013101300 A1 * | 7/2013 | ........... A61C 17/222 |

* cited by examiner

ORAL CARE IMPLEMENT

CROSS-REFERENCE TO RELATED PATENT APPLICATIONS

The present application is a U.S. national stage application under 35 U.S.C. §371 of PCT Application No. PCT/US2013/072859, filed Dec. 3, 2013, which claims the benefit of U.S. Provisional Patent Application No. 61/735,650, filed Dec. 11, 2012, the entireties of which are hereby incorporated by reference.

BACKGROUND OF THE INVENTION

Powered toothbrushes having replaceable heads, commonly referred to as replacement heads, are known in the art. Such powered toothbrushes typically include a handle and a replacement head that is detachably coupled to the handle. The replaceability of the heads in such powered toothbrushes is desirous because the handle, which includes the expensive motion-inducing circuitry and components, is expensive to manufacture and has a much longer life expectancy than do the cleaning elements, such as bristles, that are on the head. Consumers would not be willing to pay a premium to purchase such powered toothbrushes if they had to be discarded when the bristles or other cleaning elements wore out. Thus, it is now standard in the industry to provide replacement heads that can be attached to and detached from the handle so that worn out replacement heads can be replaced as needed for the same handle.

Existing replacement heads suffer from a number of deficiencies, including complexity of manufacture, the ability to improperly load the replacement head to the handle, and inadequate coupling of the replacement head to the handle. Thus, a need exist for a replacement head having an improved coupling structure.

BRIEF SUMMARY OF THE INVENTION

The present invention is directed to a replacement head for an oral care implement, such as a toothbrush, wherein the replacement head utilizes a specially designed structure for coupling the replacement head to a handle of the oral care implement handle. The handle comprises a stem having a boss extending outwardly therefrom, the boss comprising a locking section and an anti-lock section. The replacement head comprises a tubular sleeve into which the stem is disposed when the replacement head is coupled to the handle. The tubular sleeve matingly interacts with the boss of the handle such that a locking tab of the tubular sleeve contacts the locking section of the boss to axially retain the replacement head to the handle.

In one embodiment, the invention can be an oral care implement comprising: a handle comprising: a gripping portion comprising a shoulder; a stem extending from the shoulder of the gripping portion along a first longitudinal axis; and a boss protruding radially outward from an outer surface of the stem, the boss comprising a locking section having an undercut surface that is axially spaced from the shoulder and an anti-lock section extending from the locking rib section to the shoulder; and a replacement head comprising: a tubular sleeve comprising a cavity and a proximal edge defining an opening into the cavity; a protuberance protruding radially inward from an inner surface of the tubular sleeve; and a locking tab protruding radially inward from the inner surface of the tubular sleeve and circumferentially spaced from the protuberance; and the tubular sleeve detachably coupled to the stem in a locked state in which the stem is located within the cavity of the tubular sleeve, the locking tab and the protuberance are located on opposite sides of the boss, the locking tab engages the undercut surface of the boss to prevent axial disengagement of the tubular sleeve from the stem, the protuberance engages the boss to impede rotation of the tubular sleeve about the stem in a first angular direction.

In another embodiment, the invention can be a replacement head for coupling to a handle of an oral care implement, the replacement head comprising: a head having a plurality of tooth cleaning elements mounted thereto; a tubular sleeve comprising a cavity for receiving a stem of the handle, a proximal edge defining an opening into the cavity, and a distal end to which the head is coupled; a protuberance protruding radially inward from an inner surface of the tubular sleeve for engaging a boss of the stem to impede rotation of the tubular sleeve about the stem in a first angular direction; and a locking tab protruding radially inward from the inner surface of the tubular sleeve for engaging an undercut surface of the boss to prevent axial disengagement of the tubular sleeve from the stem, the locking tab circumferentially spaced from the protuberance so that an first axial channel exists therebetween for receiving a section of the boss.

In yet another embodiment, the invention can be a method of detachably coupling a replacement head to a handle of an oral care implement, the method comprising: a) positioning a replacement head in axial alignment with a stem of a handle; b) translating the stem into a cavity of the tubular sleeve via an opening; and c) rotating the tubular sleeve relative to the stem in a second rotational direction from: (1) a first rotational position in which a locking tab and a protuberance of the tubular sleeve are on the same side of a boss of the stem; to (2) a second rotational position in which the locking tab and the protuberance are located on opposite sides of the boss, the locking tab engages an undercut surface of the boss to prevent axial disengagement of the tubular sleeve from the stem, and the protuberance engages the boss to impede rotation of the tubular sleeve about the stem in a first angular direction that is opposite the second angular direction.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
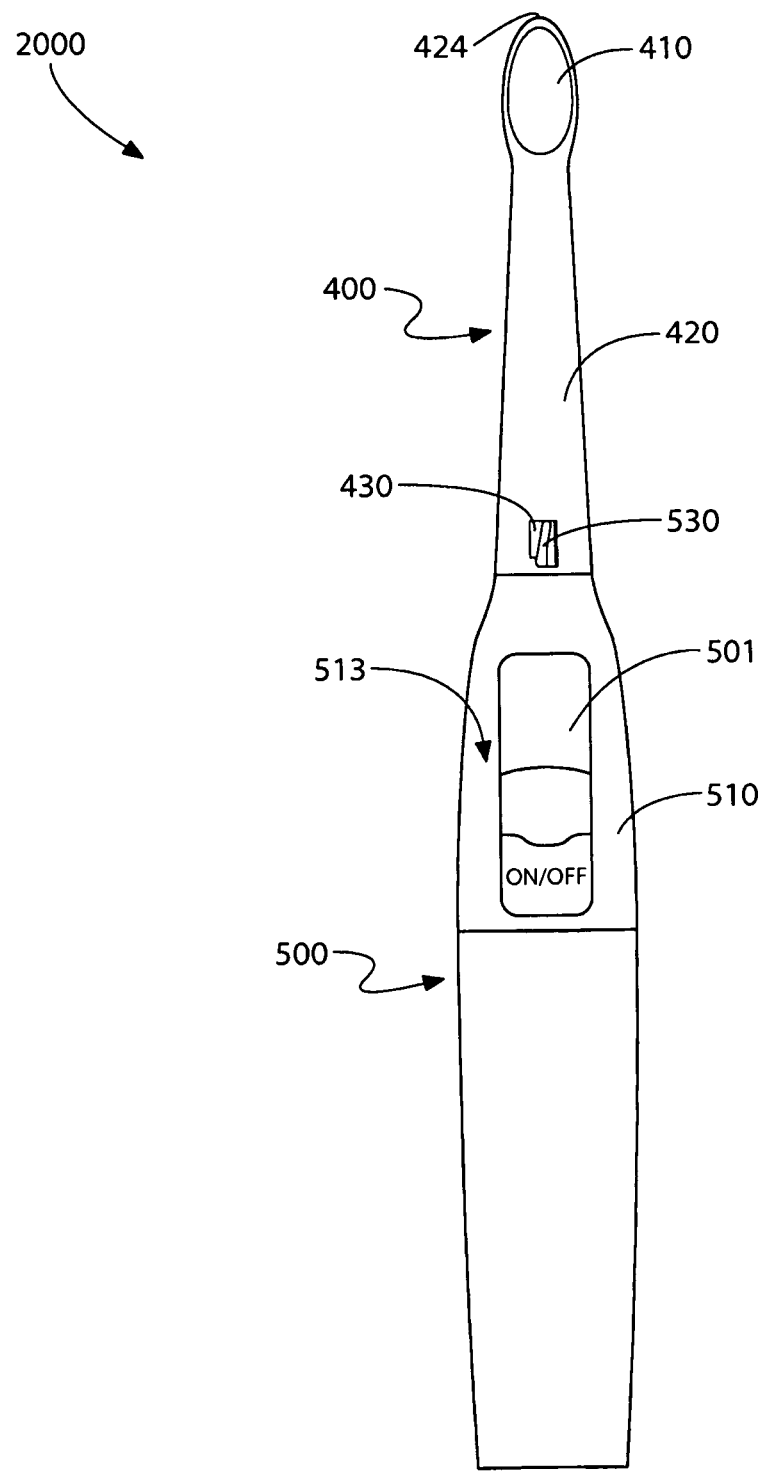
FIG. 1 is a front view of an oral care implement having a handle and a replacement head according to one embodiment of the present invention, wherein the replacement head is detachably coupled to the handle.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
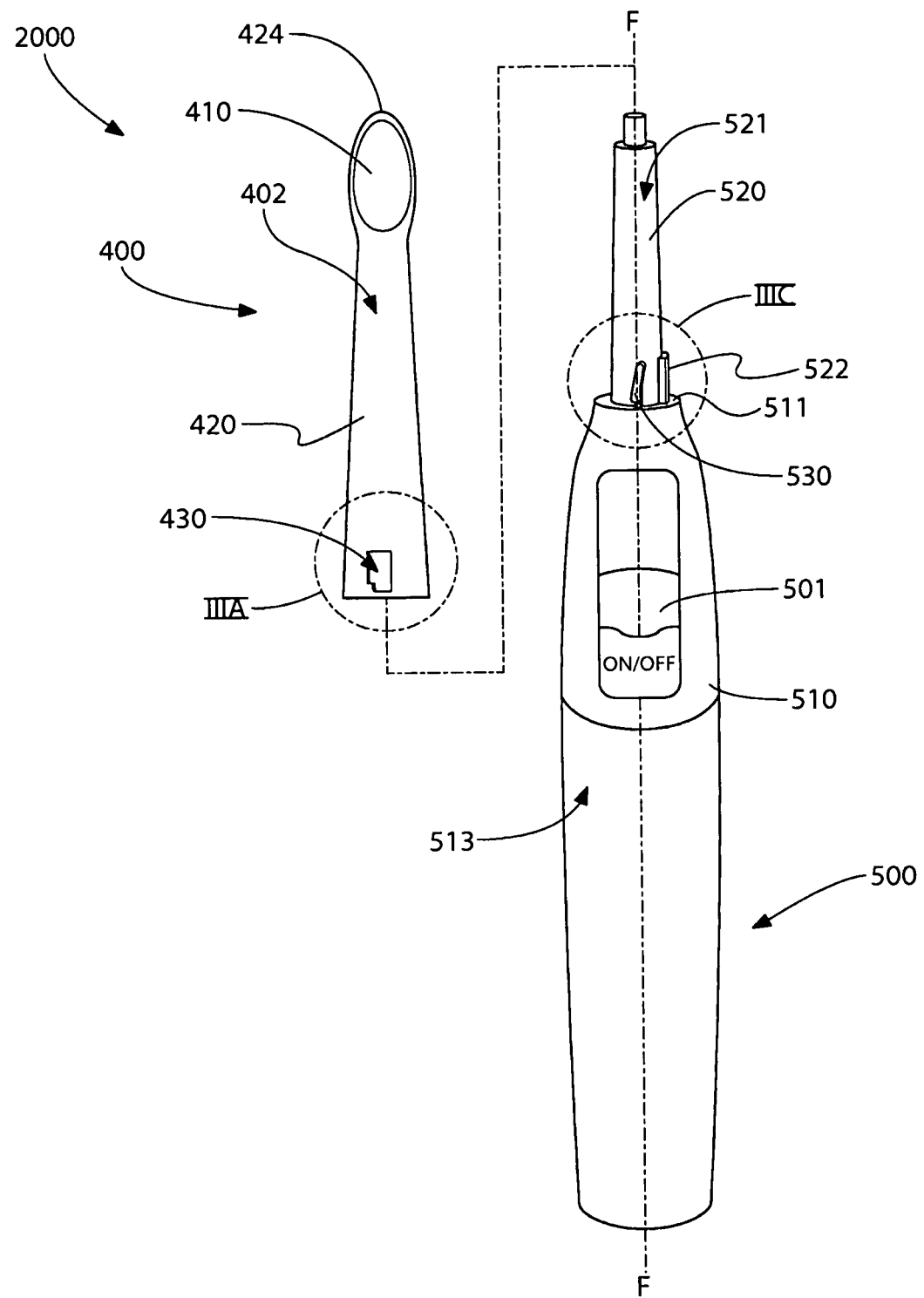
FIG. 2 is a front view of the oral care implement of FIG. 1, wherein the replacement head is detached from the handle.

Referring to FIGS. 1 and 2 concurrently, a powered toothbrush 2000 according to one embodiment of the present invention is illustrated. The powered toothbrush 2000 generally comprises a replacement head 400 and a handle 500. As discussed in greater detail below, the replacement head 400 and the handle 500 are designed so that the replacement head 400 can be repetitively coupled to and uncoupled from the handle 500. In FIG. 1, the powered toothbrush 2000 is illustrated in a state wherein the replacement head 400 is detachably coupled to the handle 500 according to an embodiment of the present invention. In FIG. 2, the powered toothbrush 2000 is illustrated in a state wherein the replacement head 400 is not coupled to the handle 500, but positioning of the replacement head 400 for detachable coupling to the handle 500 is illustrated in dotted lines.

While the invention is exemplified herein as a powered toothbrush, it is to be understood that the inventive concepts discussed herein can be applied to manual toothbrushes that utilize replacement heads, or other manual or powered oral care implements, including without limitation tongue cleaners, water picks, interdental devices, tooth polishers and specially designed ansate implements having tooth engaging elements.

The handle 500 generally comprises a gripping portion 510 and a stem 520. The gripping portion 510 terminates at a shoulder 511 at its distal end. The shoulder 511 of the handle 500 is an annular shoulder that forms a distal end of the gripping portion 510 of the handle 500. In the exemplified embodiment, the shoulder 511 is a stepped surface including the flat distal end of the gripping portion 510 of the handle and a radial collar 512 of the stem 520 (see FIG. 3C). Of course, the invention is not to be so limited in all embodiments and in certain other embodiments the shoulder 511 can be a flat surface with the radial collar 512 omitted. The stem 520 extends from the gripping portion 510, and more specifically from the shoulder 511 of the gripping portion 510, along a longitudinal axis F-F. In certain embodiments, the stem 520 and gripping portion 510 of the handle 500 are unitarily formed. However, in certain other embodiments the stem 520 and gripping portion 510 of the handle 500 can be separately formed and connected by means known in the art during a later step in the manufacturing process. In exemplified embodiments, the handle 500, including the stem 520 and gripping portion 510, are formed from a rigid plastic material such as for example without limitation polymers and copolymers of ethylene, propylene, butadiene, vinyl compounds and polyesters, such as polypropylene or polyethylene terephthalate. Of course, the invention is not to be so limited in all embodiments and other less rigid materials, including thermoplastic elastomers, can be used to form portions of the handle 500 in other embodiments.

The gripping portion 510 of the handle 500 is an elongated structure that provides the mechanism by which the user can hold and manipulate the powered toothbrush 2000 during use. The gripping portion 510 can take on a wide variety of shapes, contours and configurations, none of which are limiting of the present invention. Included within the handle 500 is a power source, an electric motor and electrical circuitry and components necessary to create a desired motion within the replacement head 400. Furthermore, in certain embodiments the handle 500, and more specifically the stem 520 of the handle 500, includes a vibratory element or other motion inducing element operably coupled to the power source for imparting the desired motion to a head and/or tooth cleaning elements of the powered toothbrush 2000 to achieve a desired cleaning of a user's teeth.

The handle 500 also includes a user interface 501 that controls the various operations of the toothbrush 2000, including without limitation turning off and on, changing speeds of the motor, or other included functions. The handle 500, in essence, forms a watertight housing for the aforementioned electrical circuit and mechanical components that need to be protected from moisture. In the exemplified embodiment, the user interface 501 includes an on/off switch on an outer surface 513 of the handle 500. The on/off switch can take many forms, including without limitation a push button, a slide switch, a touch activated switch or the like. The particular mechanism by which the powered toothbrush 2000 is powered on and off is not to be limiting of the present invention in all embodiments.

The stem 520 of the handle 500 is an elongated structure that provides the mechanism by which the replacement head 400 is detachably coupled to the handle 500. Specifically, the stem 520 of the handle 500 and the replacement head 400 comprise a mating boss/locking structure that facilitates the coupling of the replacement head 400 to the stem 520. More specifically, the handle 500 comprises a boss 530 extending radially outward from an outer surface 521 of the stem 520 and the replacement head 400 comprises a locking tab 438 and a protuberance 437 (see FIG. 4) that engage the boss 530 of the stem 520 when the replacement head 400 is detachably coupled to the handle 500 to prevent and/or limit relative rotational and/or axial movement of the replacement head 400 relative to the stem 520. Thus, the boss 530 of the handle 500 and the locking tab 438 and protuberance 437 of the replacement head 400, the details of which will be described in more detail below, facilitate detachably coupling the replacement head 400 to the handle 500.

Still referring to FIGS. 1 and 2 concurrently, the handle 500 further comprises at least one indexing rib 522 extending outwardly from the outer surface 521 of the stem 520. In certain embodiments, the handle 500 comprises two of the indexing ribs 522 extending outwardly from the outer surface 521 of the stem 520. However, the invention is not to be limited by the number of indexing ribs in all embodiments. The indexing rib 522 is configured to ensure proper rotational alignment between the replacement head 400 and the handle 500 during coupling of the replacement head 400 to the handle 500 as will be described in more detail below.

In the exemplified embodiment, the indexing rib 522 is a longitudinal boss that extends along the length of the stem 520 generally in the direction of the longitudinal axis F-F. Specifically, the indexing rib 522 extends along the stem 520 from the shoulder 511 of the gripping portion 510 a distance that is approximately 10-25% of the length of the stem 520. Of course, the invention is not to be limited by the particular arrangement, shape, length and/or positioning of the indexing rib 522 in all embodiments and the indexing rib 522 can take on any other configuration so long as it facilitates rotational alignment between the replacement head 400 and the handle 500. Thus, in certain embodiments the indexing rib 522 is a continuous protrusion extending from the outer surface 521 of the stem 520 and in other embodiments the indexing rib 522 is formed from two or more separate protrusions that are not continuously formed. In still other embodiments, the indexing rib 522 is an annular shaped boss having a gap in the region of the boss 530. Furthermore, in certain embodiments the indexing rib 522 can be altogether omitted and rotational alignment between the replacement head 400 and the handle 500 can be achieved from the boss 530 of the handle 500 and the protuberance 437/locking tab 438 of the replacement head 400.

In certain embodiments, the replacement head 400 is inventive without the handle 500 although in other embodiments the invention is the oral care implement 2000 that includes both the replacement head 400 and the handle 500. The replacement head 400 includes a head portion 410 of the powered toothbrush 2000. While not illustrated, the head portion 410 comprises a plurality of tooth cleaning elements extending from a surface thereof as is known in the art. The plurality of tooth cleaning elements is provided for cleaning and/or polishing an oral surface and/or interdental spaces of a user's mouth. The tooth cleaning elements can be particularly suited for brushing teeth, or can be particularly suited to polish teeth instead of or in addition to cleaning teeth. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements of the present invention can be connected to the replacement head 400 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Referring to FIGS. 1-3B concurrently, the replacement head 400 will be further described. The replacement head 400 comprises a tubular sleeve 420 having an inner surface 426 that defines a cavity 421 into which the stem 520 of the handle 500 is disposed when the replacement head 400 is detachably coupled to the handle 500. The cavity 421 is sized and shaped to accommodate the stem 520 of the handle 500 so that the replacement head 400 can be detachably coupled to the handle 500. The tubular sleeve 420 further comprises a proximal edge 422 that defines an opening 423 into the cavity 421. The opening 423 provides a passageway into the cavity 421 so that the stem 520 of the handle 500 can be axially translated into and out of the cavity 421 via the opening 423. Thus, during coupling of the replacement head 400 to the handle 500, the stem 520 of the handle 500 is inserted into the cavity 421 of the tubular sleeve 420 of the replacement head 400 by inserting the stem 520 through the opening 423 of the tubular sleeve 420.

The head portion 410 of the replacement head 400 forms a distal end 424 of the tubular sleeve 420. In the exemplified embodiment, the tubular sleeve 420 and the head portion 410 of the replacement head 400 are integrally formed as a single unitary structure using a molding, milling, machining or other suitable process. However, in other embodiments the head portion 410 and the tubular sleeve 420 of the replacement head 400 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. In certain embodiments, the replacement head 400 is formed of a hard plastic material, such as for example without limitation polypropylene, polymers and copolymers of ethylene, propylene, butadiene, vinyl compounds and polyesters such as polyethylene terephthalate.

A window 430 is formed into the tubular sleeve 420 of the replacement head 400. The window 430 forms an opening through the tubular sleeve 420 that extends from an outer surface 402 of the tubular sleeve 420 to the inner surface 426 of the tubular sleeve 420. The window 430 is defined by a top edge 431, a bottom edge 432, a left side edge 433 and a right side edge 434. The top edge, 431, the bottom edge 432, the left side edge 433 and the right side edge 434 collectively form a closed-perimeter edge of the window 430. In the exemplified embodiment, each of the top edge 431, the left side edge 433 and the right side edge 434 are straight edges with no contour in their shape. However, the invention is not to be so limited in all embodiments and in certain other embodiments the top, left side and right side edges 431, 433, 434 may be formed with curves, contours or the like. Thus, the exact shape of the window 430 is not to be limiting of the present invention in all embodiments. The bottom edge 432 has a stepped surface including a first horizontal wall 432a and a second horizontal wall 432b that are separated from one another by a vertical wall 432c. In the exemplified embodiment, the transition between the vertical wall 432c and the second horizontal wall 432b is an axially contoured corner 435. Of course, the invention is not to be so limited and in other embodiments the corner 435 may be a hard, 90° corner.

The replacement head 400 further comprises a strap portion 436 that extends from the bottom edge 432 of the window 430 to the proximal edge 422 of the tubular sleeve 420. The strap portion 436 forms a portion of the closed-perimeter edge of the window 430 and a portion of the proximal edge 422 of the tubular sleeve 420. The strap portion 436 is the portion of the tubular sleeve 420 that extends from the bottom edge 432 of the window 430 in the region between the left side edge 433 and the right side edge 434 of the window 430. The strap portion 436 forms a portion of the tubular sleeve 420 and thus the inner surface 426 of the tubular sleeve 420 is also the inner surface of the strap portion 436. A protuberance 437 extends radially inward from the inner surface 426 of the strap portion 436 of the tubular sleeve 420. In the exemplified embodiment, the protuberance 437 is a semi-spherically shaped projection having a convex outer surface that extends from the inner surface 426 of the strap portion 436 of the tubular sleeve 420 inwardly towards the cavity 421. Forming the protuberance 437 with a semi-spherical or otherwise contoured shape facilitates locking the replacement head 400 to the handle 500 as will be described in more detail below. In other embodiments, the protuberance 437 can have a segmented cylindrical shape. Of course, the invention is not to be particularly limited by the shape of the protuberance 437 in all embodiments. The protuberance 437 extends a first distance $D_1$ from the inner surface 426 of the strap portion 436 of the tubular sleeve 420.

The tubular sleeve 420 of the replacement head 400 includes a bottom annular portion 460, which is a portion of the replacement head 400 that includes the strap portion 436. The bottom annular portion 460 of the tubular sleeve 420 is radially resilient such that the bottom annular portion 460 can expand radially outward and transition the bottom annular portion 460 from having a circular cross-sectional shape to an ovular cross-sectional shape. The bottom annular portion 460 and its radially resilient feature will be discussed in more detail below with reference to FIGS. 6A-8B.

A locking tab 438 also extends radially inward from the inner surface 426 of the strap portion 436 of the tubular sleeve 420. The locking tab 438 extends in the axial direction from the proximal end 422 of the tubular sleeve 420 to the axially contoured corner 435 between the vertical wall 432c and the second horizontal wall 432b of the bottom wall 432. Thus, as will be described in more detail below, an upper portion of the locking tab 438 engages a portion of the boss 420 when the replacement head 400 is detachably coupled to the handle 500 to assist in axially retaining the replacement head 400 to the handle 500. The locking tab 438 extends a second distance $D_2$ from the inner surface 426 of the strap portion 436 of the tubular sleeve 420. In the exemplified embodiment, the second distance $D_2$ is greater than the first distance $D_1$ and thus the locking tab 438 extends further into the cavity 421 from the inner surface 426 of the strap portion 436 of the tubular sleeve 420 than does the protuberance 437.

The locking tab 438 is circumferentially spaced apart from the protuberance 437 thereby forming a first axial channel 439 in between the locking tab 438 and the protuberance 437. Furthermore, a second axial channel 440 is formed into the tubular sleeve 420 between the protuberance 437 and a radial wall 447. The first axial channel 439 is the portion of the tubular sleeve 420 within which at least a portion of the boss 530 is positioned or nested when the replacement head 400 is detachably coupled to the handle 500 in a locked state and the second axial channel 440 is the portion of the tubular sleeve 420 within which at least a portion of the boss 530 is positioned when the replacement head 400 is detachably coupled to the handle 500 in an unlocked state, as will be described in more detail below with reference to FIGS. 6A-8B.

In the exemplified embodiment, the first and second axial channels 439, 440 are located on opposite sides of the protuberance 437 such that the protuberance 437 is positioned in between and forms the separation between the first and second axial channels 439, 440. The first axial channel 439 has a first circumferential width $W_1$ and the second axial channel 440 has a second axial width $W_2$. The second circumferential width $W_2$ of the second axial channel 440 is greater than the first axial width $W_1$ of the first axial channel 439.

The tubular sleeve 420 of the replacement head 400 also comprises at least one indexing slot 425 that is formed between two alignment lugs 427 that extend inwardly from the inner surface 426 of the tubular sleeve 420. The indexing slot 425 facilitates properly aligning the replacement head 400 relative to the handle 500 during detachable coupling of the replacement head 400 to the handle 500 as will be described in more detail below with reference to FIGS.

6A-8B. In the exemplified embodiment, the tubular sleeve 420 comprises two of the indexing slots 425. However, the invention is not to be so limited in all embodiments and the tubular sleeve 420 may comprise just a single indexing slot 425 or more than two indexing slots 425 in other embodiments. Furthermore, in still other embodiments it is possible that the indexing slots 425 and the alignment lugs 427 can be altogether omitted and alignment of the replacement head 400 relative to the handle 500 can be achieved via the protuberance 437 and the locking tab 438. The number, location, size, configuration and positioning of the indexing rib(s) 522 of the handle 500 and the indexing slot(s) 425 of the tubular sleeve 420 are not to be limiting of the present invention in all embodiments. However, the indexing rib(s) 522 and the indexing slot(s) are arranged so as to ensure that when the tubular sleeve 420 is coupled to the handle 500, the tubular sleeve 420 is initially placed into the unlocked state.

Figure 3A:
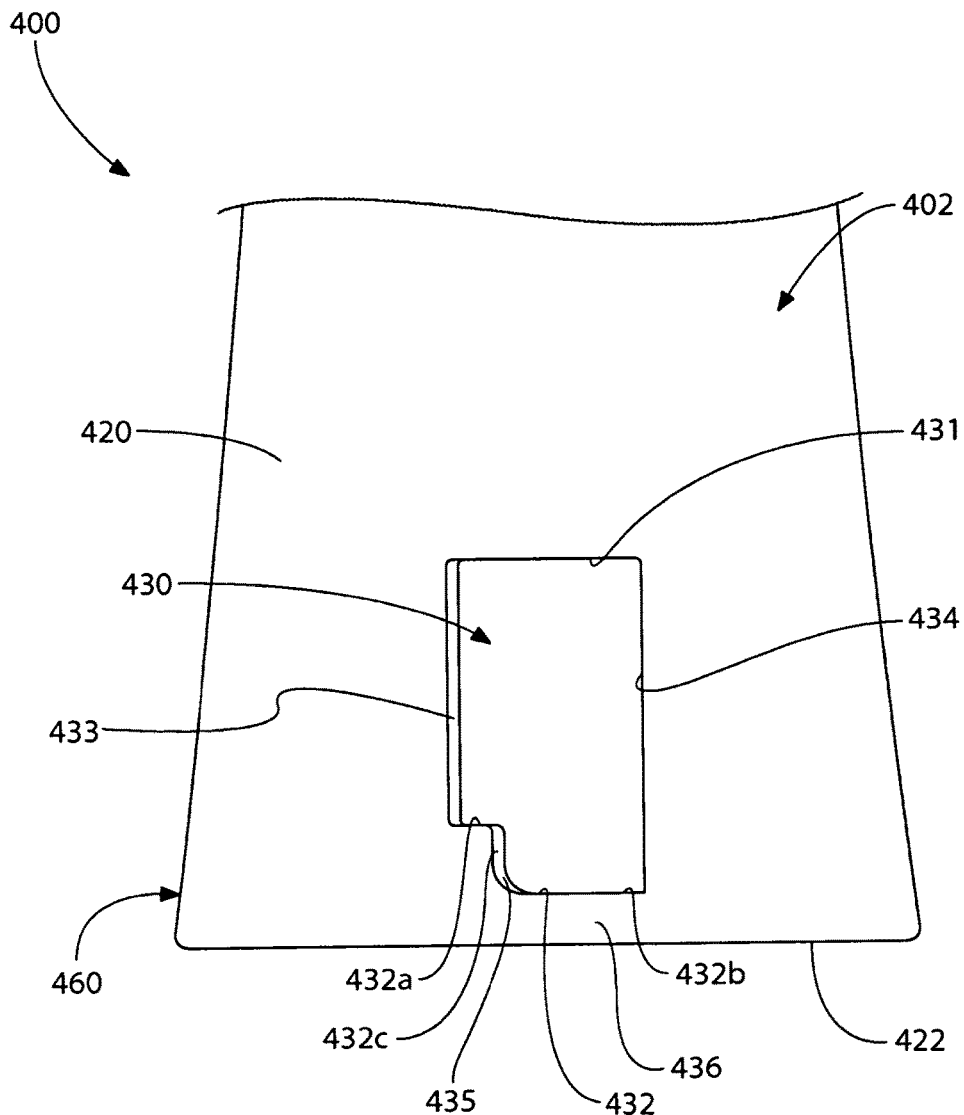
FIG. 3A is a close-up view of area IIIA of FIG. 2.
Figure 3B:
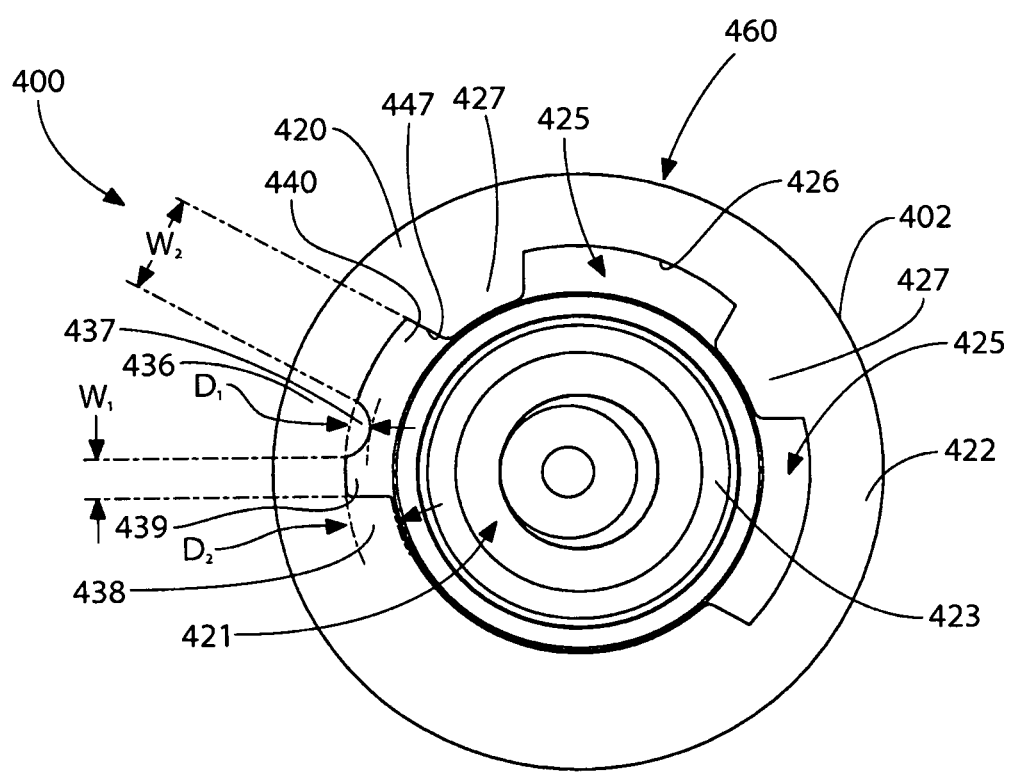
FIG. 3B is a bottom view of the replacement head.
Figure 3C:
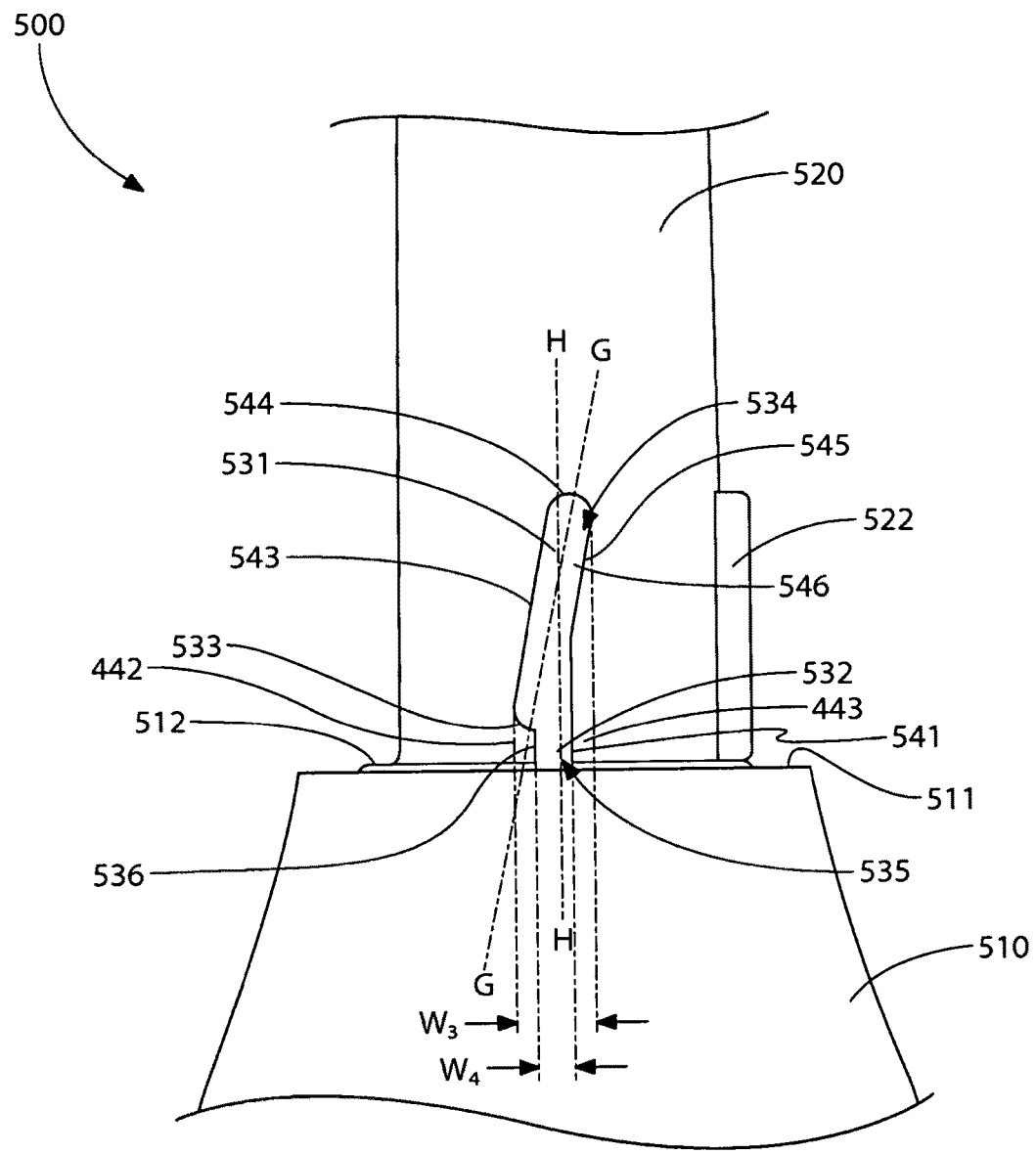
FIG. 3C is a close-up view of area IIIC of FIG. 2.

Referring now to FIGS. 2 and 3C concurrently, the boss 530 of the stem 520 of the handle 500 will be described in detail. The boss 530 generally comprises a locking section 531 and an anti-lock section 532. The locking section 531 comprises a bottom portion 533 that is axially spaced from the shoulder 511 at the distal end of the gripping portion 510. The bottom portion 533 of the locking section 531 comprises an undercut surface of the locking section 531 that is axially contoured so as to correspond in shape to the axially contoured corner 435 of the bottom wall 432 of the window 430 (and to the locking tab 438) for facilitating coupling of the replacement head 400 to the handle 500. More specifically, the bottom portion 533 of the locking section 531 of the boss 530 circumferentially protrudes from the anti-lock section 532 along a first side 442 of the boss 530. As will be discussed in more detail below, the undercut surface of the bottom portion 533 of the locking section 531 is the only undercut surface on the stem 520 that is capable of mechanically engaging a feature of the tubular sleeve 420 to prevent axial disengagement of the tubular sleeve 420 from the stem 520 when the replacement head 400 is detachably coupled to the handle 500 in the locked state.

The locking section 531 also comprises a top portion 546 that circumferentially protrudes from the anti-lock section 532 along a second side 443 of the boss 530. In the exemplified embodiment, the locking section 531 is an oblique rib section of the boss 530 in that the locking section 531 is oriented obliquely relative to the longitudinal axis F-F. Thus, in the exemplified embodiment the top portion 546 of the locking section 531 comprises an oblique lower edge. Furthermore, in the exemplified embodiment the anti-lock section 532 is an axial rib section of the boss 530 in that the anti-lock section 532 is oriented axially relative to the longitudinal axis F-F.

The boss 530 has a third circumferential width $W_3$ that is an overall circumferential width of the boss 530 extending from the outermost circumferential edge of the bottom portion 533 to the outermost circumferential edge of the top portion 546. Furthermore, the anti-lock section of the boss 530 has a fourth circumferential width $W_4$ that is smaller than the overall width $W_3$ of the boss 530. As will be discussed in greater detail below with reference to FIGS. 6A-8B, the third circumferential width $W_3$ of the boss 530 is substantially equal to the first circumferential width $W_1$ of the first axial channel 439. The fourth circumferential width $W_4$ of the anti-lock section 532 of the boss 530 is equal to or greater than the second circumferential width $W_2$ of the second axial channel 440. As used herein, the term substantially equal includes slight tolerances between the various widths that may be used to facilitate locking the tubular sleeve 420 of the replacement head 400 to the stem 520 of the handle 500 as will be described in more detail below.

The anti-lock section 532 extends from the locking section 531 in the direction of the longitudinal axis F-F and terminates into the shoulder 511. In the exemplified embodiment, the boss 530 does not protrude radially beyond the radial collar 512 of the shoulder 511. Of course, in embodiments whereby the radial collar 512 is omitted, the boss 530 does not protrude radially beyond the outer surface of the shoulder 511. Thus the boss 530, and particularly the anti-lock section 532 of the boss 530, does not have a surface that can be engaged by the tubular sleeve 420 of the replacement head 400 because the bottom surface of the anti-lock section 532 of the boss 530 terminates directly into the shoulder 511 and the boss 530 does not protrude radially beyond the outer surface of the shoulder 511.

The locking section 531 of the boss 530 comprises an outer surface 534. Similarly, the anti-lock section 532 of the boss 530 comprises an outer surface 535. There is no break or gap between the outer surface 534 of the locking section 531 and the outer surface 535 of the anti-lock section 532. Furthermore, in the exemplified embodiment the outer surface 534 of the locking section 531 and the outer surface 535 of the anti-lock section 532 extend the same distance outwardly from the outer surface 521 of the stem 520. Thus, the outer surface 534 of the locking section 531 and the outer surface 534 of the anti-lock section 532 are substantially continuous surfaces. Of course, the invention is not to be so limited in all embodiments and in certain other embodiments the distance that the outer surface 534 of the locking section 531 and the distance that the outer surface 535 of the anti-lock section 532 extend from the outer surface 521 of the stem 520 can be different.

The locking section 531 extends along a first rib axis G-G and the anti-lock section 532 extends along a second rib axis H-H. The first rib axis G-G is oriented obliquely relative to the second rib axis H-H. Furthermore, the first rib axis G-G is oriented obliquely relative to and non-intersecting with the longitudinal axis F-F of the stem 520. The locking section 531 forms an elongated and linear rib section that extends obliquely as described above. The anti-lock section 532 forms an elongated and linear rib section that extends in the direction of the longitudinal axis F-F.

The locking section 531 is defined by the bottom portion 533, a first side wall 543, a top wall 544 and a second side wall 545. The anti-lock section 532 is defined by a first side wall 536 and a second side wall 541. Furthermore, the locking section 531 and the anti-lock section 532 are separated by an imaginary line that extends from the second side wall 545 of the locking section 531 to an apex located at the transition point between the first side wall 536 of the anti-lock section 532 and the bottom portion 533 of the locking section 531. However, as noted above there is no actual distinction between the locking section 531 and the anti-lock section 532 and they are contiguous with respect to one another.

As noted briefly above, the anti-lock section 532 extends downwardly from the locking section 531 to prevent inadequate and/or improper coupling of replacement heads to the handle 500. Specifically, without the anti-lock section 532, an improperly and/or inadequately designed replacement head could be coupled to the handle 500. The inclusion of the anti-lock section 532 on the stem 520 of the handle 500 prevents improperly and/or inadequately designed replacement heads from being coupled to the handle. Thus, the anti-lock section 532 does not prevent locking of the replacement head 400 to the handle 500, but merely prevents locking of improperly and/or inadequately designed replacement heads to the handle 500, thereby preventing potential damage to handle 500 and unexpected detachment of such improper and/or inadequate replacements heads during use.

Figure 4:
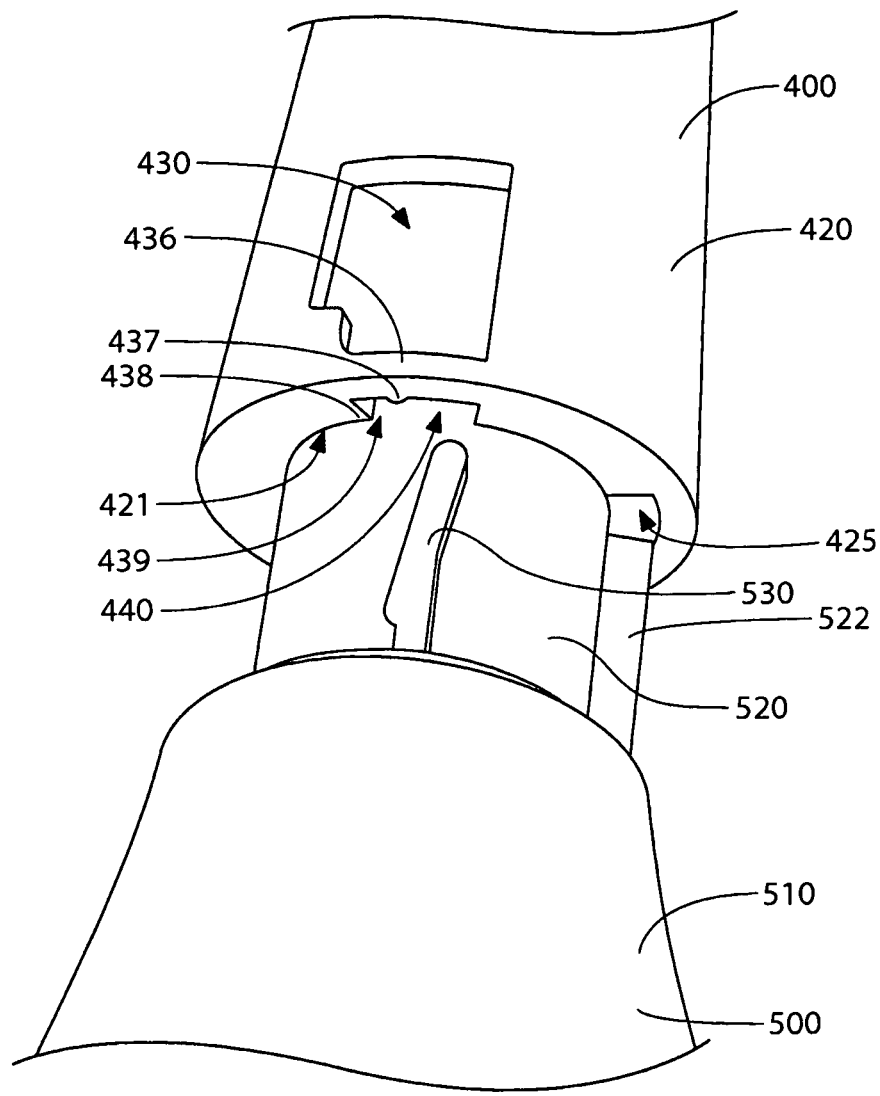
FIG. 4 is a close-up perspective view illustrating the replacement head partially coupled to the handle.
Figure 5:
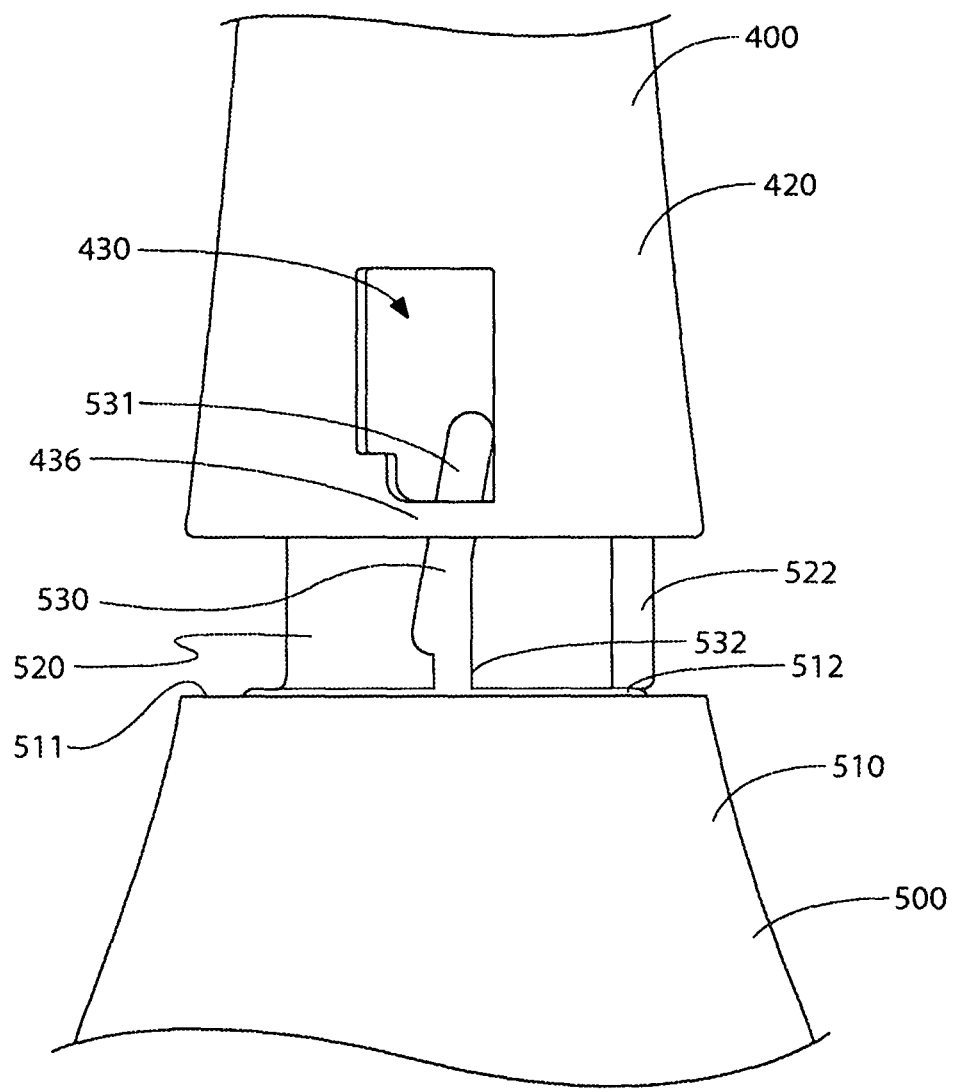
FIG. 5 is a close-up front view illustrating the replacement head partially coupled to the handle.

Referring to FIGS. 4-6A concurrently, the process of detachably coupling the replacement head 400 to the handle 500 will be described. As discussed above, in order to couple the replacement head 400 to the handle 500, proper rotational alignment between the replacement head 400 and the handle 500 is first ensured. Thus, as can be seen in FIG. 4, first the replacement head 400 is positioned into axial alignment with the stem 520 of the handle 500. As the stem 520 of the handle 500 is inserted into the cavity 421 of the replacement head 400, the indexing rib 522 of the handle 500 is axially aligned with the indexing slot 425 of the tubular sleeve 420. As a result, as the stem 520 of the handle 500 continues to be inserted into the cavity 421 of the replacement head 400, the indexing rib 522 is received within the indexing slot 425. Thus, to detachably couple the replacement head 400 to the handle 500, first the tubular sleeve 420 of the replacement head 400 is axially aligned with the stem 520 of the handle 500 and then rotated relative to the stem 520 of the handle 500 until the indexing rib 522 of the handle 500 is axially aligned with the indexing slot 425 of the tubular sleeve 420.

Figure 6A:
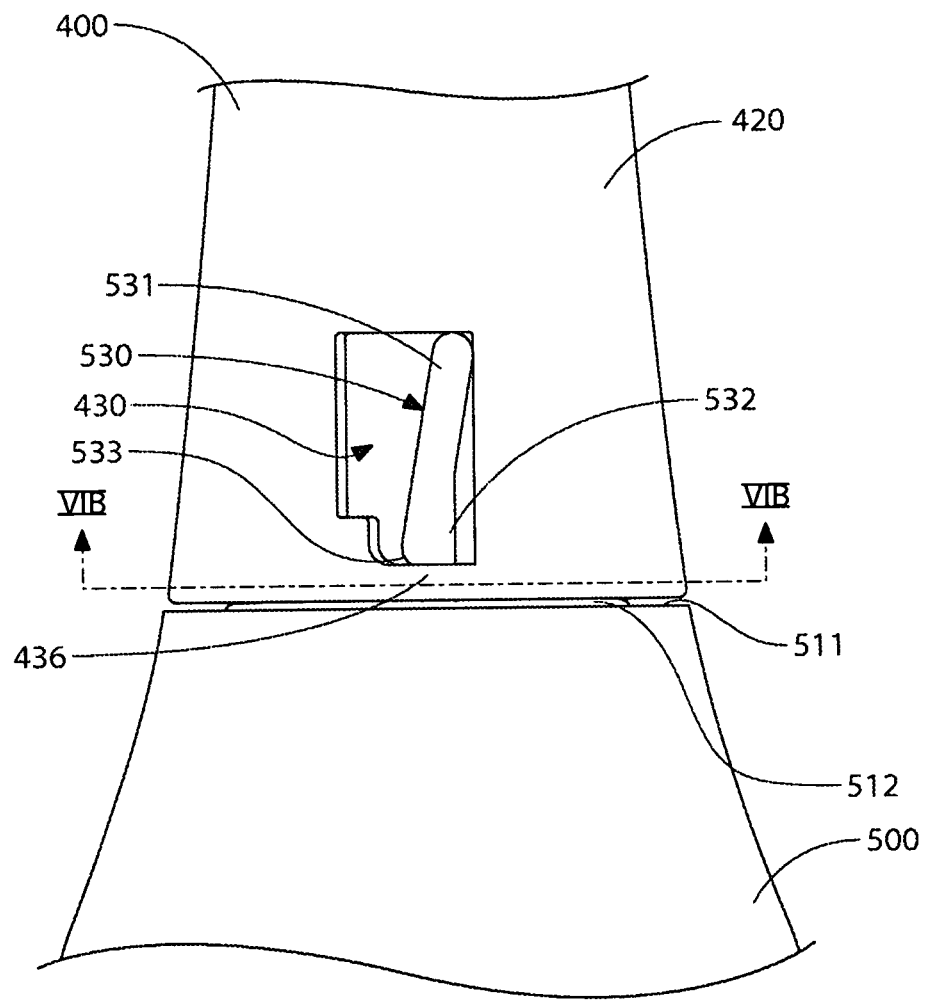
FIG. 6A is a close-up front view illustrating the replacement head detachably coupled to the handle in an unlocked state.
Figure 6B:
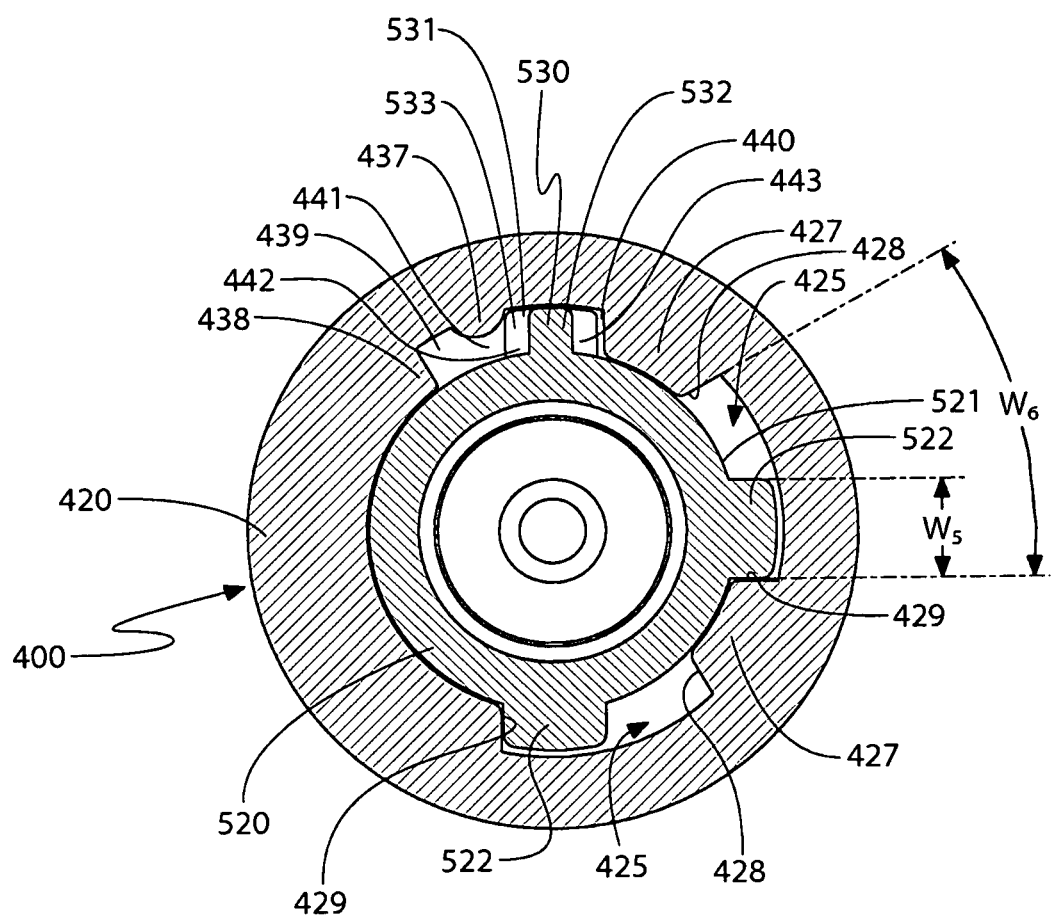
FIG. 6B is a cross-sectional view taken along line VIB-VIB of FIG. 6A.

As can be seen from FIG. 6B, in the exemplified embodiment the stem 520 of the handle 500 comprises two indexing ribs 522 and the tubular sleeve 420 of the replacement head 400 comprises two indexing slots 425. Thus, in the exemplified embodiment alignment of the replacement head 400 relative to the handle 500 is achieved when each of the indexing ribs 522 of the handle 500 is aligned with and received within a corresponding one of the indexing slots 425 of the tubular sleeve 420 of the replacement head 400.

FIG. 6B illustrates the tubular sleeve 420 positioned in a first rotational position or unlocked state relative to the handle 500. When in the unlocked state (i.e., first rotational position), each of the indexing ribs 522 engages a second radial wall 429 of the respective indexing slot 425 within which it is located. Each of the indexing ribs 522 comprises a circumferential width $W_5$ and each of the indexing slots 425 comprises a circumferential width $W_6$ such that the circumferential width $W_6$ of the indexing slots 425 is greater than the circumferential width $W_5$ of the indexing ribs 522. Due to the greater size of the circumferential width $W_6$ of the indexing slot 425 relative to the circumferential width $W_5$ of the indexing rib 522, the tubular sleeve 420 can be angularly rotated relative to the stem 520 from the first rotational position to a second rotational position (i.e., from the unlocked locked state to the locked state) and vice versa. Thus, angularly rotating the tubular sleeve 420 relative to the stem 520 in a second angular direction (i.e., counter-clockwise in the exemplified embodiment) positions the indexing ribs 522 into engagement with a first radial wall 428 of the respective indexing slot 425 within which they are located (see FIG. 8B).

Referring again to FIGS. 4-6A concurrently, upon achieving proper axial alignment of the replacement head 400 relative to the handle 500 as described above, the boss 530 of the stem 520 of the handle 500 is axially aligned with the second axial channel 440 of the tubular sleeve 420. As the stem 520 of the handle 500 continues to be inserted into the cavity 421 of the tubular sleeve 420 of the replacement head 400, the boss 530 enters into and becomes nested within the second axial channel 440. As can be seen in FIG. 6A, the stem 520 of the handle 500 is inserted into the cavity 421 of the tubular sleeve 420 until the stem 520 can be pushed no further into the cavity 421 due to contact between the proximal edge 422 of the tubular sleeve 420 and the shoulder 511 (or radial collar 512) of the handle 500. Upon such contact, the replacement head 400 is detachably coupled to the handle 500 in an unlocked state (i.e., first rotational position). Furthermore, upon such detachable coupling, the locking section 531 of the boss 530 is exposed through the window 430 of the tubular sleeve 420 and at least a portion of the anti-lock section 532 of the boss 530 is not exposed via the window 430 due to being overlaid by the strap portion 436 of the tubular sleeve 420. Furthermore, in the unlocked state (i.e., first rotational position), the entirety of the boss 530 is nested within the second axial channel 440 and the indexing ribs 522 are in contact with or adjacent to the second radial wall 429 of the indexing slots 425.

Referring to FIGS. 6A and 6B concurrently, the replacement head 400 is illustrated detachably coupled to the handle 500 in the unlocked state. In the unlocked state, the boss 530 of the handle 500 is located within the second axial channel 440 of the tubular sleeve 420. Thus, in the unlocked state both the protuberance 437 and the locking tab 438 are positioned on the first side 442 of the boss 530. Specifically, the undercut surface of the bottom portion 533 of the locking section 531 of the boss 530 is positioned adjacent to the protuberance 437. In this unlocked state, neither the protuberance 437 nor the locking tab 438 are engaged or in contact with the undercut bottom portion 533 of the locking section 531 of the boss 530. As a result, the replacement head 400 can be axially slid upwardly relative to the stem 520 of the handle 500 without any components interfering with such upward movement of the replacement head 400. Thus, the unlocked state refers to the fact that the only movement of the replacement head 400 relative to the stem 520 needed to separate the replacement head 400 from the stem 520 of the handle 500 is an axial upward sliding movement.

When the replacement head 400 is detachably coupled to the handle 500 as illustrated in FIGS. 6A and 6B, the locking tab 438 is in substantially continuous surface contact with the outer surface 521 of the stem 520. Furthermore, the protuberance 437 is spaced from the outer surface 521 of the stem 520 by a gap 441. The gap 441 facilitates enabling the boss 530 and the protuberance 437 to pass by one another when the replacement head 400 is transitioned from the unlocked state to the locked state as will be described below.

Figure 7A:
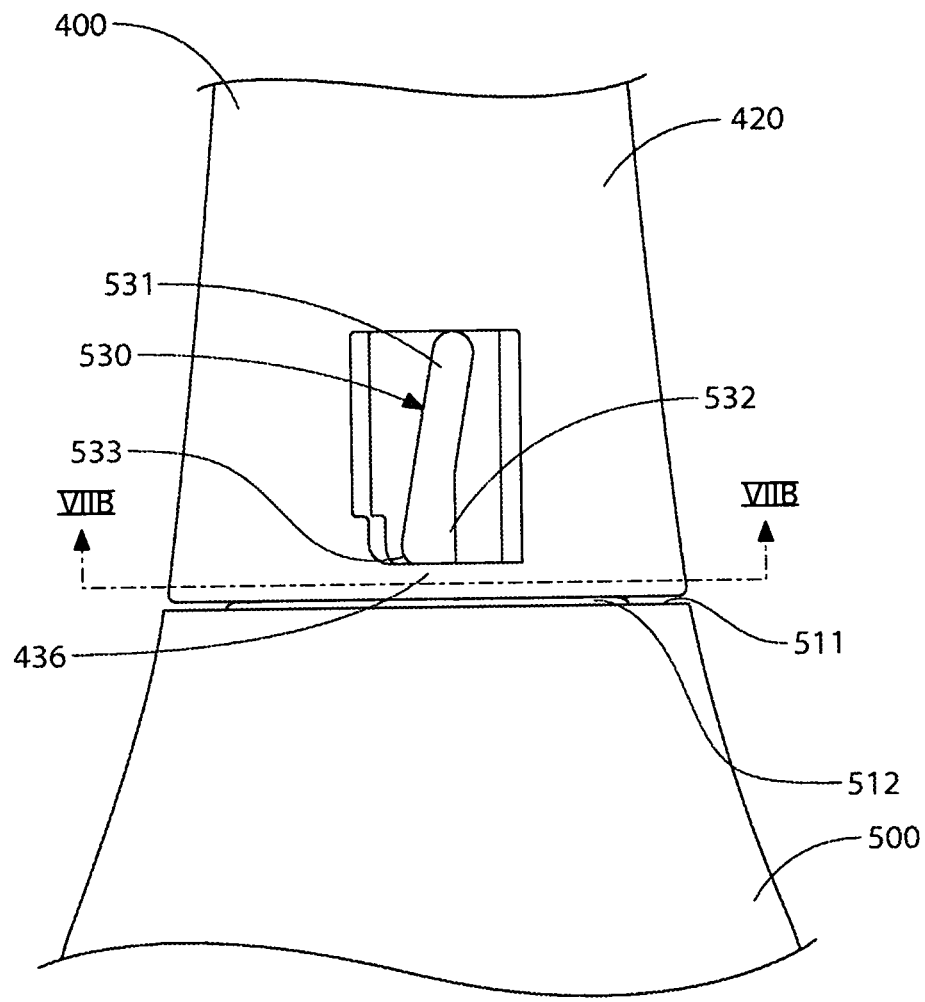
FIG. 7A is a close-up front view illustrating the replacement head detachably coupled to the handle between the unlocked state and a locked state, wherein a protuberance of the tubular sleeve is riding over an anti-lock section of the boss.
Figure 7B:
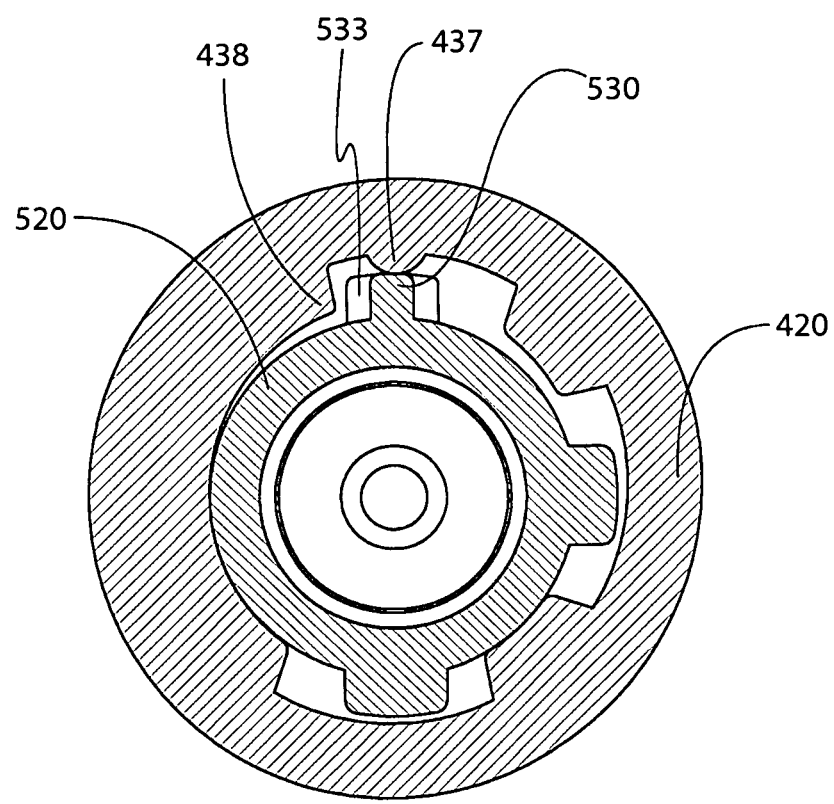
FIG. 7B is a cross-sectional view taken along line VIIB-VIIB of FIG. 7A.
Figure 8A:
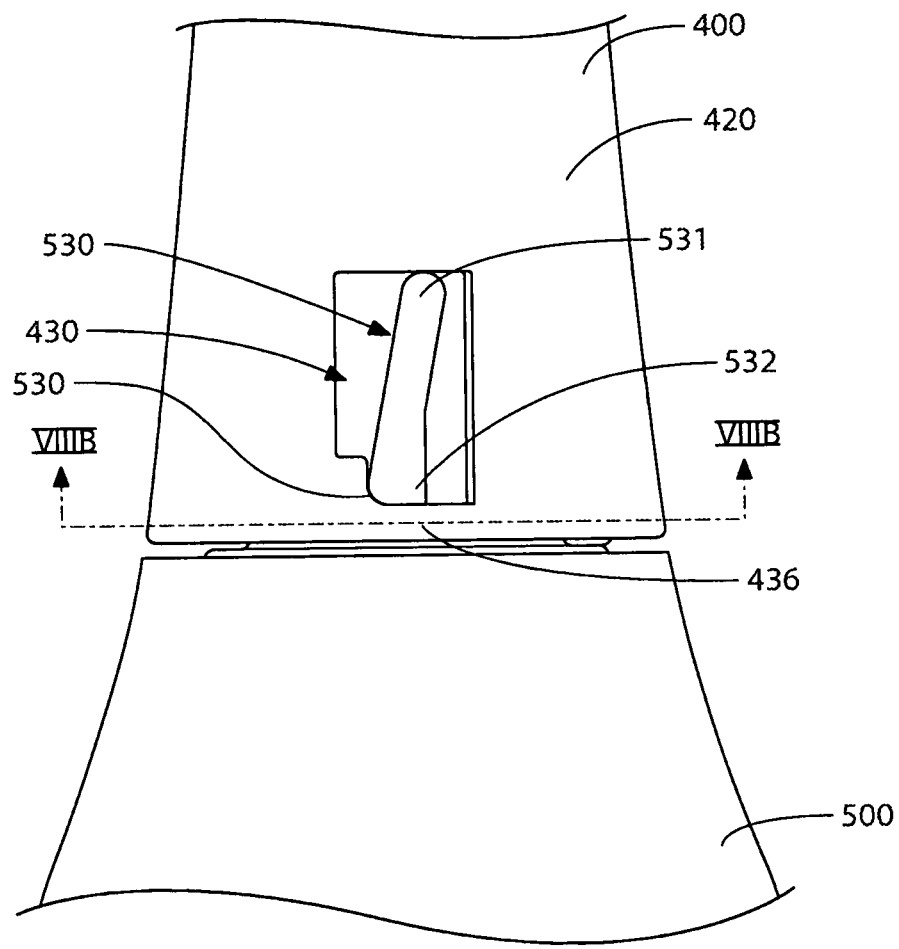
FIG. 8A is a close-up front view illustrating the replacement head detachably coupled to the handle in the locked state.
Figure 8B:
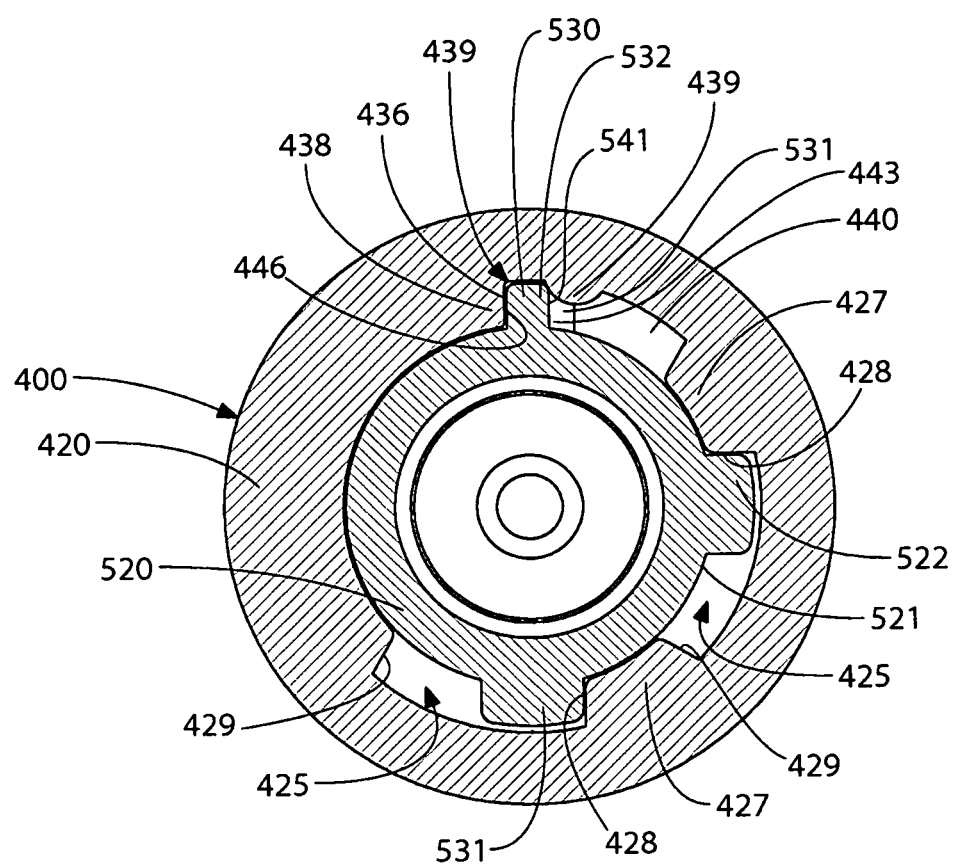
FIG. 8B is a cross-sectional view taken along line VIIIB-VIIIB of FIG. 8A.

Referring to FIGS. 6A-8B concurrently, transitioning from the unlocked state to the locked state will be described. After the replacement head 400 is fully positioned onto the stem 520 of the handle 500 such that the proximal end 422 of the tubular sleeve 420 contacts the shoulder 511 (or radial collar 512) of the handle 500, the tubular sleeve 420 is rotated in a second angular direction relative to the stem 520. In the exemplified embodiment, transitioning from the unlocked state illustrated in FIGS. 6A-6B to the locked state illustrated in FIGS. 8A-8B is achieved by rotating the tubular sleeve 420 in a counter-clockwise direction relative to the stem 520 of the handle 500. However, the invention is not to be so limited in all embodiments and clockwise rotation of the tubular sleeve 420 may be used in certain other embodiments to achieve the locking state.

During transitioning from the unlocked state to the locked state (i.e., from the first rotational position to the second rotational position), the protuberance 437 rides over the anti-lock section 532 of the boss 530 as illustrated in FIGS. 7A and 7B. This is achieved due to the radial resiliency of the bottom annular section 460 of the tubular sleeve 420 discussed above. Specifically, as the protuberance 437 rides over the anti-lock section 532 of the boss 530, the bottom annular section 460 of the tubular sleeve 420 radially expands. More specifically, while the protuberance 437 rides over the anti-lock section 532 of the boss 530, the annular section 460 of the tubular sleeve 420 radially deforms from a normal state (illustrated in FIG. 6B) to a flexed state (illustrated in FIG. 7B). As the protuberance 437 rides over the anti-lock section 532 of the boss 530, the tubular sleeve 420 continues to be angularly rotated in the manner discussed above until the tubular sleeve 420 reaches the locked state (i.e., second rotational position) whereby the protuberance 437 snaps back toward the stem 520 after passing over the anti-lock section 532 of the boss 530. Upon the tubular sleeve 420 reaching the second rotational position, the bottom annular section 460 of the tubular sleeve 420 returns to the normal state (illustrated in FIG. 8B).

After passing over the anti-lock section 532 of the boss 530, the protuberance 437 is positioned on the second side 443 of the boss 530 and the locking tab 438 remains on the first side 442 of the boss 530, the second side 443 being opposite the first side 442. Thus, in the locked position the boss 530, and specifically the anti-lock section 532 of the boss 530, is positioned within and extends through the first axial channel 439 located in between the protuberance 437 and the locking tab 438. As noted above, in the exemplified embodiment the protuberance 437 is semi-spherically shaped and has a convex outer surface. The semi-spherical shape of the protuberance 437 facilitates enabling the protuberance 437 to pass over the anti-lock section 532 of the boss 530. Specifically, the spherical shape of the protuberance 437 provides a ramped surface for facilitating passing the protuberance 437 along and over the anti-lock section 532 of the boss 530.

Although not visible in FIG. 8B, in the locked state an upper surface of the locking tab 438 engages the undercut surface of the bottom portion 533 of the locking section 531 of the boss 530 to assist in axially retaining the replacement head 400 to the handle 500 and to prevent axial disengagement of the tubular sleeve 420 from the stem 520. Specifically, the locking tab 438 extends inwardly towards the cavity 421 from the inner surface 426 of the tubular sleeve 420 and provides a ledge or extension of the tubular sleeve 420 that engages with the bottom portion 533 of the locking section 531 of the boss 530 such that the replacement head 400 cannot be slid axially relative to the handle 500 to separate the replacement head 400 from the handle 500 when the replacement head 400 and handle 500 are detachably coupled and in the locked state. Furthermore, a side surface 446 of the locking tab 438 engages the first side wall 536 of the anti-lock section 532 of the boss 530 to prevent over-rotation of the tubular sleeve 420 relative to the stem 520 in the second angular direction.

Similarly, in the locked state the protuberance 437 engages the boss 530 to impede rotation of the tubular sleeve 420 about the stem 520 in a first angular direction. The first angular direction is opposite the second angular direction, and thus the first angular direction transitions the replacement head 400 relative to the handle 500 from the unlocked state to the locked state. Specifically, the protuberance 437 engages the second side wall 541 of the anti-lock section 532 of the boss 530 to impede rotation of the tubular sleeve 420 relative to the stem 520 in the first angular direction. Thus, the protuberance 437 facilitates maintaining the replacement head 400 coupled to the handle 500 in the locked state. The protuberance 437 does not completely prevent rotation of the tubular sleeve 420 about the stem 520 in the first angular direction, but merely impedes such angular rotation so that the tubular sleeve 420 is not readily separated from the stem 520 of the handle 500 without a purposeful rotation of the tubular sleeve 420 in the first angular direction. Thus, when it is desired to transition the connection between the replacement head 400 and the handle 500 from the locked state to the unlocked state, a user can rotate the tubular sleeve 420 in the first angular direction such that the protuberance 437 rides back over the anti-lock section 532 of the boss 530 and becomes repositioned on the first side 442 of the boss 530.

As noted above, in the locked state the locking tab 438 engages the first side wall 536 of the anti-lock section 532 of the boss to prevent over-rotation of the tubular sleeve 420 relative to the stem 520 in the second angular direction. Furthermore, the indexing ribs 522 engage the first radial wall 428 of the indexing slots 425 to also prevent over-rotation of the tubular sleeve 420 relative to the stem 520 in the second angular direction.

The locking section 531 of the boss 530 is exposed or visible through the window 130 of the tubular sleeve 420 in both the unlocked state and the locked state. Furthermore, at least a portion of the anti-lock section 532 (i.e., the portion of the anti-lock section 532 that extends axially below the bottom portion 533 of the locking section 531) is overlaid by the strap portion 436 of the tubular sleeve 420 in both the unlocked state and the locked state. When in the unlocked state, the entirety of the boss 530 is positioned within the second axial channel 440. Furthermore, when in the locked state, at least a portion of the boss 530 is positioned within the first axial channel 439. Specifically, in the locked state at least the anti-lock section 532 of the boss 530 is positioned within the first axial channel 439.

After use of the replacement head 400 for a desired period of time, it is common for a user to exchange the replacement head 400 for another one of the replacement heads 400. Thus, in order to transition from the locked state to the unlocked state, the replacement head 400 is rotated relative to the handle 500 in the opposite direction from that discussed above with regard to transitioning from the unlocked state to the locked state. Thus, if the replacement head 400 is rotated counter-clockwise to transition from the unlocked state to the locked state, the replacement head 400 is rotated clockwise to transition from the locked state to the unlocked state, and vice versa. After transitioning into the unlocked state, the replacement head 400 can be detached from the handle 500 by sliding the replacement head 400 upwardly in the axial direction away from the stem 520 of the handle 500.

Figure 9A:
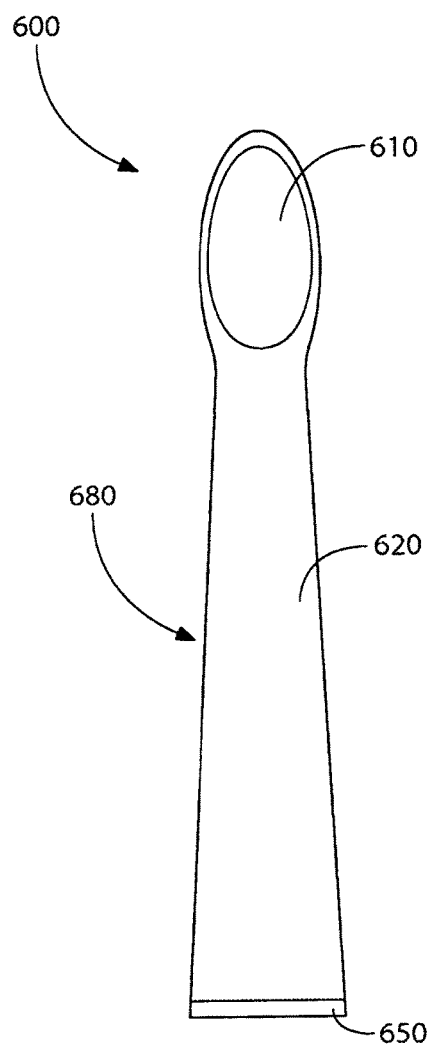
FIG. 9A is a front view of a replacement head in accordance with a second embodiment of the present invention.
Figure 9B:
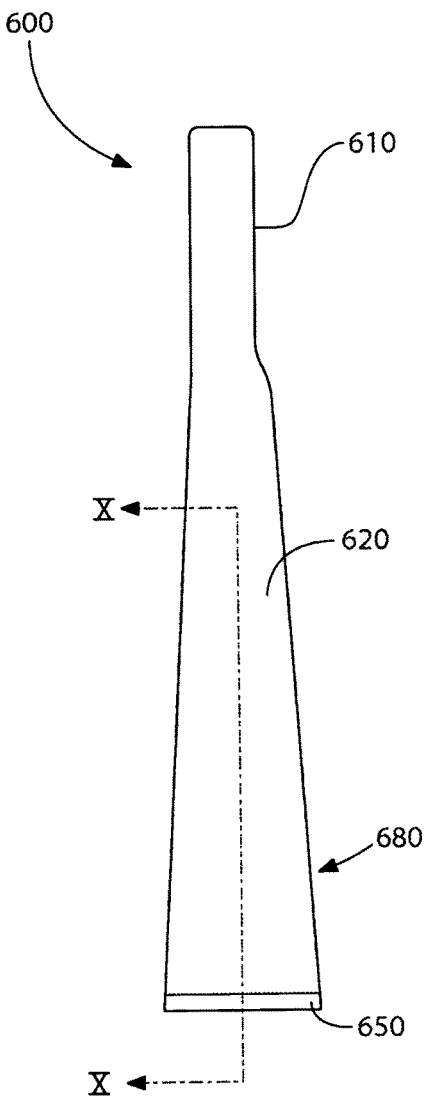
FIG. 9B is a side view of the replacement head of FIG. 9A.
Figure 10:
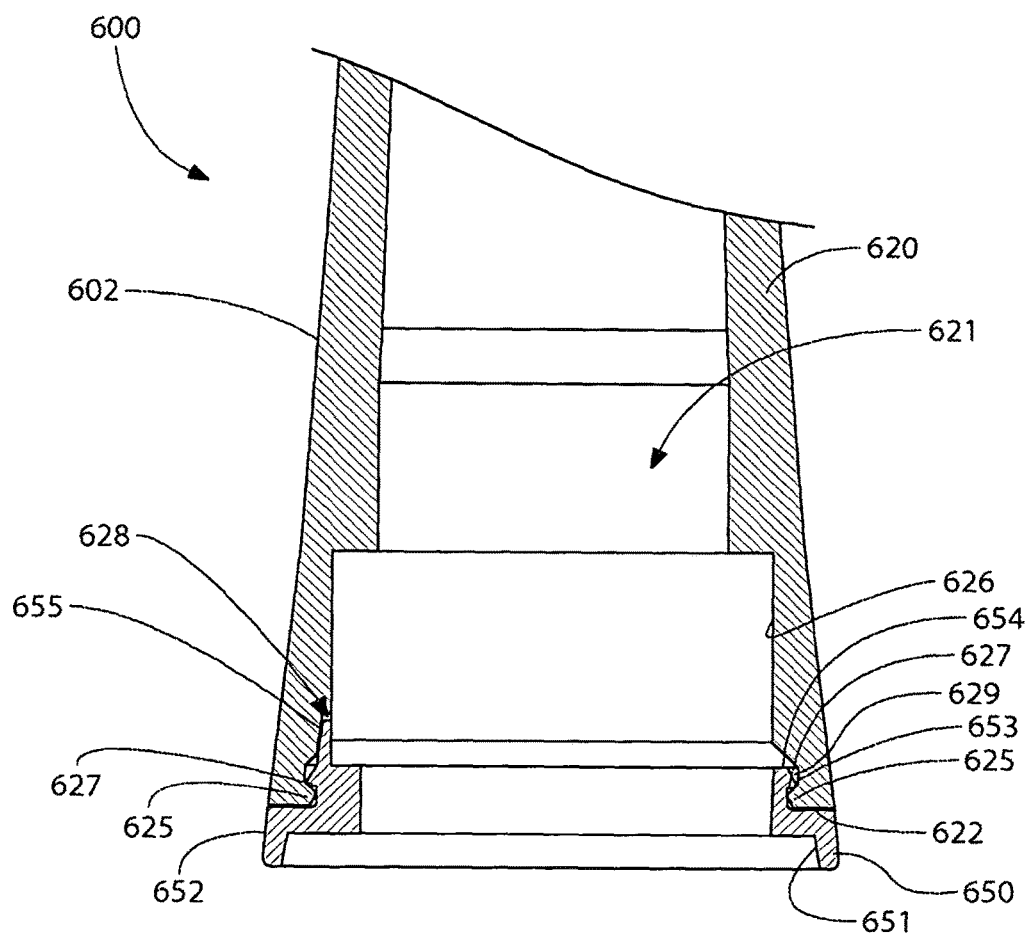
FIG. 10 is a cross-sectional view taken along line X-X of FIG. 9B.

Referring now to FIGS. 9A, 9B and 10, a replacement head 600 in accordance with another embodiment of the present invention will be described. The replacement head 600 is similar to the replacement head 400 in many respects, and thus components of the replacement head 600 that are the same as components of the replacement head 400 will not be repeated for brevity. Features of the replacement head 600 that are similar to or the same as features of the replacement head 400 will be described using the same reference numerals, except that the 600-series of numbers will be used.

The replacement head 600 comprises a head portion 610, a tubular sleeve 620 and a collar 650. The collar 650 forms a portion of the tubular sleeve 620 and thus the tubular sleeve 620 comprises a main body 680 and the collar 650 which is non-rotatably coupled to the main body 680. The collar 650 is snap-fitted onto the main body 680 to form the tubular sleeve 620. The head portion 610 and tubular sleeve 620 of the replacement head 600 are generally the same as the head portion 410 and tubular sleeve 420 of the replacement head 400 except as described in detail below. The tubular sleeve 620 comprises an outer surface 602 and an inner surface 626 that defines a cavity 621 into which the stem 520 of the handle 500 is inserted during detachable coupling the replacement head 600 to the handle 500 as described in detail above.

The tubular sleeve 620 comprises a proximal end 622, which forms a flat, bottom surface of the tubular sleeve 620. An annular flange 625 extends inwardly towards the cavity 621 at the proximal end 622 of the tubular sleeve 620. The annular flange 625 forms a top, undercut surface 627 to which the collar 650 is detachably coupled as will be described in detail below. Furthermore, the tubular sleeve 620 comprises an annular recess 629 that also facilitates coupling the collar 650 thereto as will be described in more detail below. The tubular sleeve 620 also comprises an indexing slot 628 that facilitates properly aligning the collar 650 with the tubular sleeve 620 during detachable coupling of the collar 650 to the tubular sleeve 620. The indexing slot 628 is a recess formed into the tubular sleeve 620 that forms an empty space for disposal or positioning of an alignment rib of the collar 650 as will be described in more detail below.

Figure 11A:
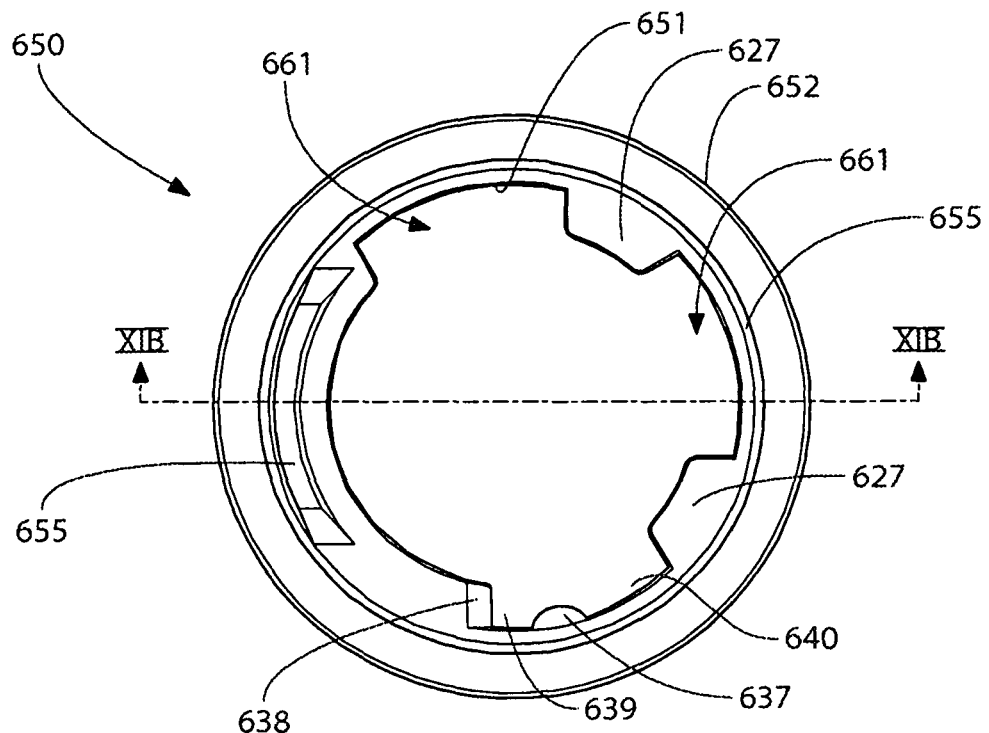
FIG. 11A is a top view of a collar of the replacement head of FIG. 9A.
Figure 11B:
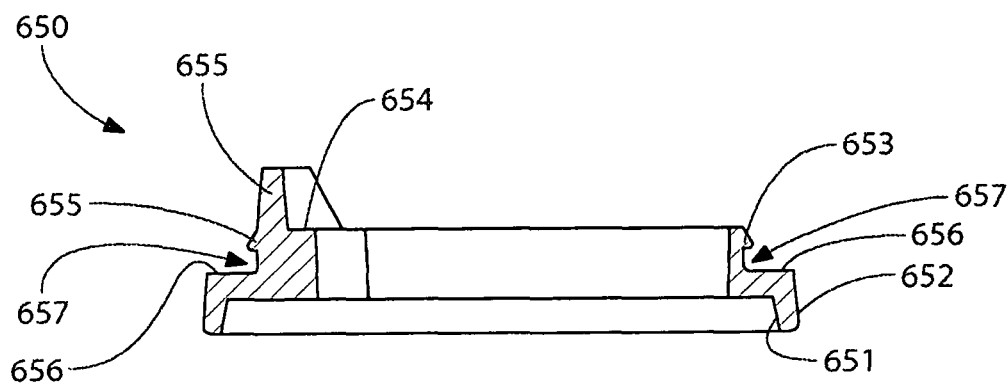
FIG. 11B is a cross-sectional view taken along line XIB-XIB of FIG. 11A.

Referring to FIGS. 10-11B concurrently, the collar 650 will be further described. The collar 650 comprises an inner surface 651 that defines a portion of the cavity 621 and an outer surface 652. An annular flange 656 extends from the outer surface 652 of the collar 650 at a top end 654 of the collar 650. Furthermore, an indexing rib 655 extends upwardly from the top surface 654 of the collar 650. Specifically, the indexing rib 655 is an arcuate shaped rib that extends upwardly from the top surface 654 of the collar 650 along a portion of one side of the collar 650. As noted above, the indexing rib 655 is received by and fits within the indexing slot 628 of the tubular sleeve 620 when the collar 650 is detachably coupled to the tubular sleeve 620. The indexing rib 655 prevents relative rotation and facilitates achieving proper rotational alignment between the collar 650 and the main body 680 of the tubular sleeve 620.

The collar 650 comprises a shoulder 656 and an annular recess 657 positioned between the shoulder 656 and the annular flange 653. In order to detachably couple the collar 650 to the tubular sleeve 620, the collar 650 is pressed upwardly against the proximal end 622 of the tubular sleeve 620 and rotated until the indexing rib 655 of the collar 650 is rotationally aligned with the indexing slot 628 of the tubular sleeve 620. Once such alignment is achieved, the collar 650 snap-fits into the tubular sleeve 620 such that the annular flange 655 of the collar 650 fits within the annular recess 629 of the tubular sleeve 620 (i.e., of the main body portion 680 of the tubular sleeve 620). The annular flange 655 is in surface contact with the undercut top surface 627 of the annular flange 625 of the tubular sleeve 620. Furthermore, the annular flange 625 of the tubular sleeve 620 fits within the annular recess 657 of the collar 650. The shoulder 656 of the collar 650 abuts against the proximal end 622 of the tubular sleeve 620. When the collar 650 is detachably coupled to the tubular sleeve 620, the outer surface 652 of the collar 650 forms a continuous surface with the outer surface 602 of the tubular sleeve 620.

Referring now solely to FIG. 11A, the collar 650 comprises the components that facilitate coupling of the replacement head 600 to the handle 500 as has been described in detail above with regard to the replacement head 400. The collar 650 comprises at least one indexing slot 661 that is formed between two alignment lugs 627 that extend inwardly from the inner surface 651 of the collar 650. The indexing slots 661 facilitate properly aligning the replacement head 600 relative to the handle 500 during detachable coupling of the replacement head 600 to the handle 500. In the exemplified embodiment, the collar 650 comprises two of the indexing slots 661. However, the invention is not to be so limited in all embodiments and the collar 650 may comprise a single indexing slot 661 or more than two indexing slots 661 in other embodiments. Further, in still other embodiments the indexing slots 661 can be altogether omitted.

Furthermore, the collar 650 comprises a protrusion 637 extending radially inward from the inner surface 651 of the collar. In the exemplified embodiment, the protrusion 637 is a semi-spherically shaped projection having a convex outer surface that extends from the inner surface 651 of the collar 650. Forming the protrusion 637 with a semi-spherical or otherwise contoured shape facilitates locking the replacement head 600 to the handle 500. In other embodiments, the protuberance 637 may have a segmented cylindrical shape.

A locking tab 638 also extends radially inward from the inner surface 651 of the collar 650. The locking tab 638 is similar to the locking tab 438 described above in that it engages a bottom edge 533 of the boss 530 of the handle (FIG. 3C) when the replacement head 600 is detachably coupled to the handle 500. The locking tab 638 is circumferentially spaced apart from the protrusion 637 thereby forming a first axial channel 639 between the locking tab 638 and the protrusion 637. Furthermore, a second axial channel 640 is formed into the collar 650 between the protrusion 637 and one of the alignment lugs 627.

The replacement head 600 is detachably coupled to the handle 500 in much the same way as described above with regard to attachment of the replacement head 400 to the handle 500. The difference is that the collar 650 comprises the protrusion 637 and the locking tab 638 rather than those components being formed directly into the tubular sleeve 620. Furthermore, the replacement head 600 does not include a window. Of course, in certain embodiments the replacement head 600 can include a window as has been described above with regard to the replacement head 400. In embodiments wherein the tubular sleeve 620 does not include a window, the tubular sleeve 620 may include at least one recess formed into its inner surface for accommodating the boss 530 and/or any of the indexing ribs 522 therein when the tubular sleeve 620 is detachably coupled to the handle 500.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
   a handle comprising:
   a gripping portion comprising a shoulder;
   a stem extending from the shoulder of the gripping portion along a first longitudinal axis; and
   a boss protruding radially outward from an outer surface of the stem, the boss comprising a locking section having an undercut surface that is axially spaced from the shoulder and an anti-lock section extending from the locking section to the shoulder, wherein the anti-locking section comprises an outer surface and the locking section comprises an outer surface, the outer surface of the anti-locking section and the outer surface of the locking section being the same surface; and
   a replacement head comprising:
   a tubular sleeve comprising a cavity and a proximal edge defining an opening into the cavity;
   a protuberance protruding radially inward from an inner surface of the tubular sleeve; and
   a locking tab protruding radially inward from the inner surface of the tubular sleeve and circumferentially spaced from the protuberance; and
   the tubular sleeve detachably coupled to the stem in which the stem is located within the cavity of the tubular sleeve wherein the tubular sleeve is rotatable relative to the stem of the handle between an unlocked state and a locked state, the locked state in which the locking tab and the protuberance are located on opposite sides of the boss, the locking tab engages the undercut surface of the boss to prevent axial disengagement of the tubular sleeve from the stem, the protuberance engages the boss to impede rotation of the tubular sleeve about the stem in a first angular direction.

2. The oral care implement according to claim 1 wherein the locking section of the boss comprises a bottom portion comprising the undercut surface, the bottom portion of the locking section circumferentially protruding from the anti-lock section along a first side of the boss and the protuberance engaging a second side of the boss, the first side opposite the second side.

3. The oral care implement according to claim 2 wherein the locking section of the boss comprises a top portion circumferentially protruding from the anti-lock section along the second side of the boss, wherein the top portion comprises an oblique lower edge.

4. The oral care implement according to claim 1 wherein the locking tab engages the first side of the boss to prevent over-rotation of the tubular sleeve relative to the stem in a second angular direction that is opposite the first angular direction.

5. The oral care implement according to claim 1 wherein the protuberance protrudes a first distance from the inner surface of the tubular sleeve and the locking tab extends a second distance from the inner surface of the tubular sleeve, the second distance being greater than the first distance.

6. The oral care implement according to claim 1 wherein a first axial channel exists between the protuberance and the locking tab, the anti-lock section of the boss nesting within the first axial channel.

7. The oral care implement according to claim 6 wherein a second axial channel exists between the protuberance and a radial wall of the tubular sleeve, the first and second axial channels located on opposite sides of the protuberance, wherein the first axial channel has a circumferential width and the second axial channel has a circumferential width that is greater than the circumferential width of the first axial channel.

8. The oral care implement according to claim 1 wherein the tubular sleeve comprises at least one indexing slot, the stem comprises at least one indexing rib protruding radially outward from the outer surface of the stem, the at least one indexing rib located within the at least one indexing slot and engaging a first radial wall of the at least one indexing slot to prevent over-rotation of the tubular sleeve relative to the stem in a second angular direction that is opposite the first angular direction.

9. The oral care implement according to claim 8 wherein the at least one indexing rib has a circumferential width and the at least one indexing slot has a circumferential width, the circumferential width of the at least one indexing slot being greater than the circumferential width of the at least one indexing rib so that the tubular sleeve can be rotated relative to the stem to an unlocked state in which the at least one indexing rib contacts a second radial wall of the at least one indexing slot.

10. The oral care implement according to claim 1 wherein the locking tab comprises an upper surface that engages the undercut surface of the locking section of the boss to prevent axial disengagement of the tubular sleeve from the stem.

11. The oral care implement according to claim 1 wherein the tubular sleeve comprises a window defined by a closed-perimeter edge, the tubular sleeve comprising a strap portion.

12. The oral care implement of claim 11 wherein the strap portion forms a portion of the closed-perimeter edge of the window and a portion of the proximal edge of the tubular sleeve, and wherein the protuberance is located on the strap portion.

13. The oral care implement according to claim 11 wherein the locking section of the boss is exposed through the window and the strap portion overlays the anti-lock section.

14. The oral care implement according to claim 1 wherein a bottom annular section of the tubular sleeve is radially resilient, the bottom annular section comprising the protuberance and the locking tab.

15. The oral care implement of claim 14 wherein the bottom annular section is sufficiently radially resilient such that the tubular sleeve can be rotated in the first radial direction relative to the stem so that the protuberance rides over the anti-lock section of the boss and snaps back toward the stem after the protuberance passes over the anti-lock section of the boss.

16. The oral care implement according to claim 1 wherein the protuberance has a convex surface.

17. The oral care implement according to claim 1 wherein the locking tab is in contact with the outer surface of the stem and the protuberance is spaced from the outer surface of the stem by a gap.

18. The oral care implement according to claim 1 wherein the locking section is an oblique rib and the anti-lock section is an axial rib.

19. The oral care implement according to claim 18 wherein the oblique rib extends along a first rib axis and the axial rib extends along a second rib axis, the first rib axis oriented obliquely to the second rib axis, the first rib axis oriented obliquely relative to and non-intersecting with the first longitudinal axis.

20. The oral care implement according to claim 1 wherein the tubular sleeve is rotatable relative to the stem of the handle between: (1) the locked state; and (2) the unlocked state in which the protuberance and the locking tab are both positioned on the same side of the anti-lock section of the boss and the tubular sleeve can be slid axially relative to the stem to remove the replacement head from the handle.

21. The oral care implement according to claim 20 wherein the protuberance passes over the anti-lock section of the boss during rotation between the unlocked state and the locked state.

22. The oral care implement according to claim 1 wherein the replacement head comprises a head having a plurality of tooth cleaning elements mounted thereto and the handle comprises a motion inducing element for imparting motion to the plurality of tooth cleaning elements.

* * * * *